(12) United States Patent
Shogbon et al.

(10) Patent No.: US 9,238,794 B2
(45) Date of Patent: *Jan. 19, 2016

(54) SYNTHETIC SURFACES FOR CULTURING STEM CELL DERIVED OLIGODENDROCYTE PROGENITOR CELLS

(71) Applicant: Asterias Biotherapeutics, Inc., Menlo Park, CA (US)

(72) Inventors: Christopher Bankole Shogbon, Corning, NY (US); Yue Zhou, Horseheads, NY (US); Ralph Brandenberger, Palo Alto, CA (US)

(73) Assignee: Asterias Biotherapeutics, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/946,032

(22) Filed: Jul. 19, 2013

(65) Prior Publication Data

US 2014/0134729 A1 May 15, 2014

Related U.S. Application Data

(63) Continuation of application No. 12/362,250, filed on Jan. 29, 2009, now Pat. No. 8,513,009.

(60) Provisional application No. 61/063,010, filed on Jan. 30, 2008.

(51) Int. Cl.
  *C12N 5/079* (2010.01)
  *C12N 5/071* (2010.01)
  *C12N 5/00* (2006.01)

(52) U.S. Cl.
  CPC ............ *C12N 5/0622* (2013.01); *C12N 5/0068* (2013.01); *C12N 2500/90* (2013.01); *C12N 2506/02* (2013.01); *C12N 2533/30* (2013.01)

(58) Field of Classification Search
  CPC ............... C12N 5/0068; C12N 5/0622; C12N 2533/30; C12N 2506/02; C12N 2500/99; C12N 5/0696; C12N 2506/45; A61K 35/545
  USPC ......................................... 435/368, 366, 402
  See application file for complete search history.

(56) References Cited

U.S. PATENT DOCUMENTS

| | | | |
|---|---|---|---|
| 5,830,651 A * | 11/1998 | Cauley et al. | 435/6.16 |
| 8,513,009 B2 * | 8/2013 | Shogbon et al. | 435/368 |
| 2005/0019747 A1 * | 1/2005 | Anderson et al. | 435/4 |

FOREIGN PATENT DOCUMENTS

EP  0373626 A2  6/1990

OTHER PUBLICATIONS

Zhang et al. Stem Cells & Development, 15: 943-952, 2006.*
Mallon. The International Journal of Biochemistry and Cell Biology, 38: 1063-1075, 2006.*
Ahmed, Hydrogels: Preparation, characterization, and applications, 2013 J. Adv. Res., published online Jul. 18 2013, available at http://dx.doi.org/10.1016/j.jare.2013.07.006.
Ngyen, Photopolymerizable hydrogels for tissue engineering applications, 2002 Biomaterials 23, pp. 4307-4314.

* cited by examiner

*Primary Examiner* — Thaian N Ton
(74) *Attorney, Agent, or Firm* — Krista P. Kauppinen; E. Stewart Mittler

(57) ABSTRACT

Synthetic surfaces suitable for culturing stem cell derived oligodendrocyte progenitor cells contain acrylate polymers formed from one or more acrylate monomers. The acrylate surfaces, in many cases, are suitable for culturing stem cell derived oligodendrocyte progenitor cells in chemically defined media.

8 Claims, 10 Drawing Sheets

(A) 123-2

(B) 95-2

(C) Matrigel (A) 123-2

(B) 122-3

(C) Matrigel

Matrigel 22-2

22-3

133-4

24-10

72-2

SYNTHETIC SURFACES FOR CULTURING STEM CELL DERIVED OLIGODENDROCYTE PROGENITOR CELLS

PRIORITY

This application is a continuation of U.S. patent application Ser. No. 12/362,250, filed Jan. 29, 2009 (now U.S. Pat. No. 8,513,009), which claims priority to U.S. provisional application No. 61/063,010, filed Jan. 30, 2008. The priority applications are hereby incorporated herein by reference in their entireties.

FIELD

The present disclosure relates to cell culture articles and methods of use thereof, and more particularly to articles for supporting the culture of stem cell derived oligodendrocyte progenitor cells.

BACKGROUND

Pluripotent stem cells, such as human embryonic stem cells (hESCs) have the ability to differentiate into any of the three germ layers, giving rise to any adult cell type in the human body. This unique property provides a potential for developing new treatments for a number of serious cell degenerative diseases, such as diabetes, spinal cord injury, heart disease and the like. For example, spinal cord damage is generally irreversible with current treatments, leaving approximately 250,000 Americans in a devastating position. However, as stem cell research has developed, new exciting possibilities have arisen for people suffering from spinal cord injury. ES cell-derived neural cells have been used by researchers to treat nervous system disorders in animal models. In earlier work, researchers showed that mouse ES cells could be stimulated to differentiate into neural cells that, when transplanted into mice with neurological disorders, helped to restore normal function.

However there remain obstacles in the development of such hESC-based treatments. Such obstacles include obtaining and maintaining adequate numbers of undifferentiated hESCs in tissue culture and controlling their differentiation in order to produce specific cell types. Stem cell cultures, such as hESC cell cultures are typically seeded with a small number of cells from a cell bank or stock and then amplified in the undifferentiated state until differentiation is desired for a given therapeutic application To accomplish this, the hESC or their differentiated cells are currently cultured in the presence of surfaces or media containing animal-derived components, such as feeder layers, fetal bovine serum, or MATRIGEL®. These animal-derived additions to the culture environment expose the cells to potentially harmful viruses or other infectious agents which could be transferred to patients or compromise general culture and maintenance of the hESCs. In addition, such biological products are vulnerable to batch variation, immune response and limited shelf-life.

Some steps have been taken to culture hESCs either in media or on surfaces that are free of animal-derived components. However, the response of hESCs or their differentiated derivatives is difficult to predict as components of the surface or culture medium change. Yet some advances have been made. For example, hESC-derived oligodendrocyte progenitor cells (OPCs) have been cultured in defined serum-free medium. While such culture systems are not completely xeno-free culture systems when the matrices employed contain animal-derived components, such as gelatin and MATRIGEL, they do provide a step toward the eventual clinical application of hESC-derived OPCs. By way of further example, some synthetic surfaces have been identified that can support differentiation of human epithelial stem cells into epithelial cells. However, the systems employed relied on serum medium for the cell culture, which still potentially causes problem as described before for all biological animal derived components. To date, a completely animal free system employing a chemically defined medium and a synthetic surface has not yet been identified for culturing stem cells or cells derived from stem cells.

BRIEF SUMMARY

The present disclosure describes, inter alia, synthetic surfaces useful in the culture of stem cell-derived OPCs in chemically defined media.

In an embodiment, a method for culturing oligodendrocyte progenitor cells is provided. The method includes depositing a suspension containing the oligodendrocyte progenitor cells on a polymer material and culturing the deposited oligodendrocyte progenitor cells in a cell culture medium. The polymer material comprises a homopolymer or copolymer of selected one or more acrylate monomers.

In an embodiment, a culture of oligodendrocyte progenitor cells is provided. The culture includes an article having a polymer material disposed on a surface. The culture further includes the oligodendrocyte progenitor cells disposed on the polymer material and a culture medium in which the oligodendrocyte progenitor cells are cultured. The polymer material comprises a homopolymer or copolymer of selected one or more acrylate monomers.

In an embodiment, a cell culture article for culturing oligodendrocyte progenitor cells in a chemically defined medium is provided. The article includes a substrate having a surface and a polymer material disposed on the surface. The polymer material comprises a homopolymer or copolymer of selected one or more acrylate monomers.

One or more of the various embodiments presented herein provide one or more advantages over prior surfaces for culturing stem cell-derived OPCs. For example, the synthetic surfaces reduce potential contamination issues associated with surfaces having components obtained from or derived from animal sources. Such surfaces may also provide for improved shelf life compared to those surfaces with biological components. The ability to culture stem cell-derived OPCs in chemically-defined media further reduces potential contamination issues. In addition, there will likely be less batch to batch variation in the ability of the synthetic surfaces or chemically defined media, resulting in improved reproducibility of culture results and expectations. These and other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Unless stated otherwise, ratios of compounds in a composition, such as a solution, are stated on a by volume basis.

As used herein, "have", "having", "include", "including", "comprise", "comprising" or the like are used in their open ended sense, and generally mean "including, but not limited to".

The present disclosure describes, inter alia, articles having synthetic surfaces for culturing stem cell-derived OPCs and methods for culturing stem cell-derived OPCs on such surfaces. In some embodiments, the synthetic surfaces are used in combination with a chemically defined medium to culture stem cell-derived OPCs. The surfaces may be useful in differentiating stem cells, such as hESCs, into OPCs or for proliferating such stem cell-derived OPCs.

1. Cell Culture Article

Figure 1A:
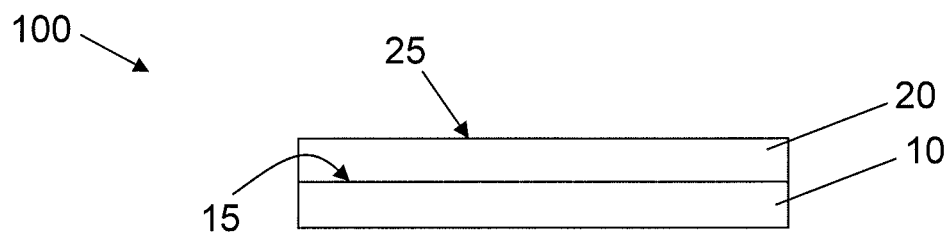
FIGS. 1A-B are schematic diagrams of side views of synthetic polymer layer coated articles.

Referring to FIG. 1, a schematic diagram of article 100 for culturing cells is shown. The article 100 includes a base material substrate 10 having a surface 15. A synthetic polymer coating layer 20 is disposed on the surface 15 of the base material 10. While not shown, it will be understood that synthetic polymer coating 20 may be disposed on a portion of base material 10. The base material 10 may be any material suitable for culturing cells, including a ceramic substance, a glass, a plastic, a polymer or co-polymer, any combinations thereof, or a coating of one material on another. Such base materials 10 include glass materials such as soda-lime glass, pyrex glass, vycor glass, quartz glass; silicon; plastics or polymers, including dendritic polymers, such as poly(vinyl chloride), poly(vinyl alcohol), poly(methyl methacrylate), poly(vinyl acetate-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like.

Examples of articles 100 suitable for cell culture include single and multi-well plates, such as 6, 12, 96, 384, and 1536 well plates, jars, petri dishes, flasks, beakers, plates, roller bottles, slides, such as chambered and multichambered culture slides, tubes, cover slips, cups, spinner bottles, perfusion chambers, bioreactors, CekSTACKs® and fermenters.

Synthetic polymer coating 20 provides a surface 25 on which cells may be cultured. The synthetic polymer surface 20 includes polymerized acrylate monomers, selected from the group of monomers provided in Table 1 below. Other materials (not shown), such as peptides, may be incorporated into or conjugated to synthetic polymer surface to produce a biomimetic surface.

TABLE 1

List of acrylate monomers

| Monomer name | Monomer structure |
|---|---|
| Tetra(ethylene glycol) diacrylate | $(H_2C=CH-C(O)-OCH_2CH_2OCH_2CH_2)_2O$ |
| Glycerol dimethacrylate | $H_2C=C(CH_3)-C(O)-OCH_2CH(OH)CH_2O-C(O)-C(CH_3)=CH_2$ |
| Triethylene glycol dimethacrylate | $H_2C=C(CH_3)-C(O)-(OCH_2CH_2)_3O-C(O)-C(CH_3)=CH_2$ |

TABLE 1-continued

List of acrylate monomers

| Monomer name | Monomer structure |
|---|---|
| 1,4-Butanediol dimethacrylate | $H_2C{=}C(CH_3){-}C(O){-}OCH_2CH_2CH_2CH_2O{-}C(O){-}C(CH_3){=}CH_2$ |
| Poly(ethylene glycol) diacrylate, $M_n{\sim}258$ | $H_2C{=}CH{-}C(O){-}(OCH_2CH_2)_n{-}O{-}C(O){-}CH{=}CH_2$ |
| 1,6-Hexanediol diacrylate | $\left(H_2C{=}CH{-}C(O){-}OCH_2CH_2CH_2{-}\right)_2$ |
| 3-Hydroxy-2,2-dimethylpropyl 3-hydroxy-2,2-dimethylpropionate | $H_2C{=}CH{-}C(O){-}OCH_2{-}C(CH_3)_2{-}C(O){-}OCH_2{-}C(CH_3)_2{-}CH_2O{-}C(O){-}CH{=}CH_2$ |
| Neopentyl glycol propoxylate (1PO/OH) diacrylate | $H_2C{=}CH{-}C(O){-}O(C_3H_6O)_mCH_2{-}C(CH_3)_2{-}CH_2(OC_3H_6)_nO{-}C(O){-}CH{=}CH_2$ <br> $m+n{\sim}2$ |
| Di(ethylene glycol) diacrylate | $H_2C{=}CH{-}C(O){-}OCH_2CH_2OCH_2CH_2O{-}C(O){-}CH{=}CH_2$ |
| Di(ethylene glycol) dimethacrylate | $H_2C{=}C(CH_3){-}C(O){-}OCH_2CH_2OCH_2CH_2O{-}C(O){-}C(CH_3){=}CH_2$ |
| Tetra(ethylene glycol) dimethacrylate | $H_2C{=}C(CH_3){-}C(O){-}OCH_2CH_2OCH_2CH_2OCH_2CH_2OCH_2CH_2O{-}C(O){-}C(CH_3){=}CH_2$ |
| 1,6-Hexanediol propoxylate diacrylate | $H_2C{=}CH{-}C(O){-}O{-}(C_3H_6O)_n{-}CH_2CH_2CH_2{-}$ <br> $H_2C{-}CH{-}C(O){-}O{-}(C_3H_6O)_n{-}CH_2CH_2CH_2{-}$ |
| Glycerol 1,3-diglycerolate diacrylate | $H_2C{=}CH{-}C(O){-}OCH_2CH(OH)CH_2OCH_2CH(OH)CH_2OCH_2CH(OH)CH_2O{-}C(O){-}CH{=}CH_2$ |
| Neopentyl glycol diacrylate | $H_2C{=}CHC(O)OCH_2{-}C(CH_3)_2{-}CH_2OC(O)CH{=}CH_2$ |
| Neopentyl glycol dimethacrylate | $H_2C{=}C(CH_3){-}C(O){-}OCH_2{-}C(CH_3)_2{-}CH_2O{-}C(O){-}C(CH_3){=}CH_2$ |

TABLE 1-continued

List of acrylate monomers

| Monomer name | Monomer structure |
| --- | --- |
| Trimethylolpropane benzoate diacrylate | |
| Trimethylolpropane ethoxylate (1 EO/OH) methyl | |
| Tricyclo[5.2.1.0$^{2,6}$]-decanedimethanol diacrylate | |
| Neopentyl glycol ethoxylate diacrylate | |
| Trimethylolpropane triacrylate | |
| 1,6-Hexanediol ethoxylate diacrylate M$_n$~314 | |
| 2,2,3,3,4,4,5,5 octafluoro 1,6 hexanediol diacrylate | |
| Poly(propylene glycol) diacrylate | n~7 |
| 1,9 nonanediol diacrylate | |

The acrylates listed in Table 1 may be synthesized as known in the art or obtained from a commercial vendor, such as Polysciences, Inc., Sigma Aldrich, Inc., and Sartomer, Inc.

Figure 1B:
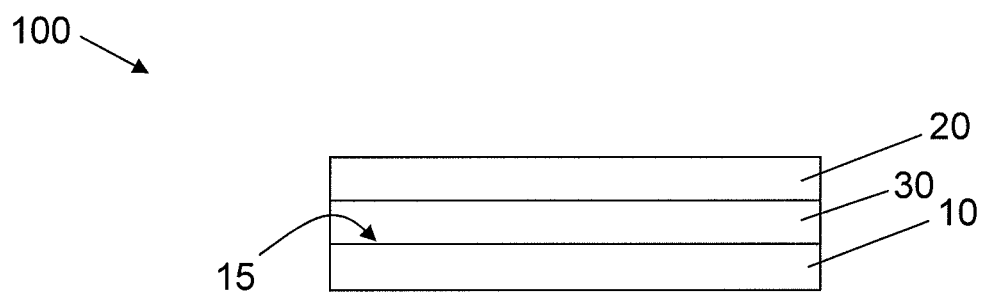

As shown in FIG. 1B, an intermediate layer 30 may be disposed between surface 15 of base material 10 and the synthetic polymer coating 20. Intermediate layer 30 may be configured to improve binding of coating 20 to substrate 10, to facilitate monomer spreading, to render portions of the surface 10 that are uncoated cytophobic to encourage cell growth on coated areas, to provide a substrate compatible with a monomer or solvent where the monomer or solvent is incompatible with the base material 10, to provide topographical features if desired through, for example, patterned printing, or the like. For example, if substrate 10 is a glass substrate, it may be desirable to treat a surface of the glass substrate with a silane molecule or an epoxy coating. For various polymer base materials 10 it may be desirable to provide an intermediate layer 30 of polyamide, polyimide, polypropylene, polyethylene, or polyacrylate. While not shown, it will be understood that synthetic polymer coating 20 may be disposed on a portion of intermediate layer 30. It will be further understood that intermediate layer 30 may be disposed on a portion of base material 10.

In various embodiments, surface 15 of base material 10 is treated, either physically or chemically, to impart a desirable property or characteristic to the surface 15. For example, and as discussed below, surface 15 may be corona treated or plasma treated. Examples of vacuum or atmospheric pressure plasma include radio frequency (RF) and microwave plasmas both primary and secondary, dielectric barrier discharge, and corona discharge generated in molecular or mixed gases including air, oxygen, nitrogen, argon, carbon dioxide, nitrous oxide, or water vapor.

Synthetic polymer coating layer 20, whether disposed on an intermediate layer 30 or base material 10, preferably uniformly coats the underlying substrate. By "uniformly coated", it is meant that the layer 20 in a given area, for example a surface of a well of a culture plate, completely coats the area at a thickness of about 5 nm or greater. While the thickness of a uniformly coated surface may vary across the surface, there are no areas of the uniformly coated surfaces through which the underlying layer (either intermediate layer 30 or base material 10) is exposed. Cell responses across non-uniform surfaces tend to be more variable than cell responses across uniform surfaces.

Synthetic polymer coating layer 20 may have any desirable thickness. However, it has been found that thicker coatings, e.g. coatings of greater than about 10 micrometers, tend to have unevenness around the periphery of the coating due to surface tension. In various embodiments, the thickness of the coating layer 20 is less than about 10 micrometers. For example, the thickness may be less than about 5 micrometers, less than about 2 micrometers, less than about 1 micrometers, less than about 0.5 micrometers or less than about 0.1 micrometers.

The polymer material forming synthetic polymer layer 20 may be cross-linked to any suitable degree. Higher degrees of cross-linking may result in reduced waste product and reduced cell toxicity.

Figure 2A:
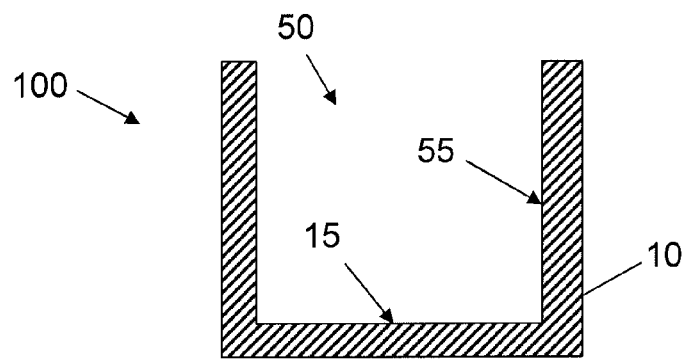
FIG. 2A-C are schematic diagrams of cross sections of cell culture articles having a well. Uncoated (2A); coated surface (2B); and coated surface and side walls (2C).
Figure 2B:
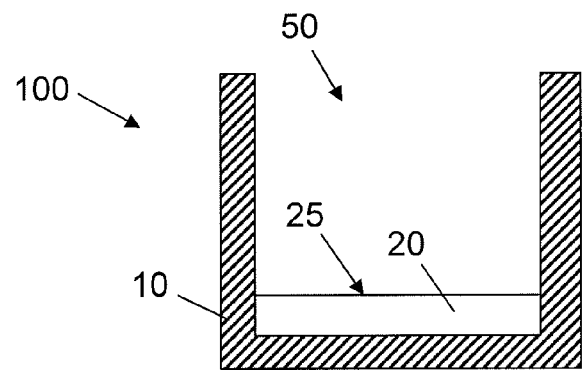
Figure 2C:
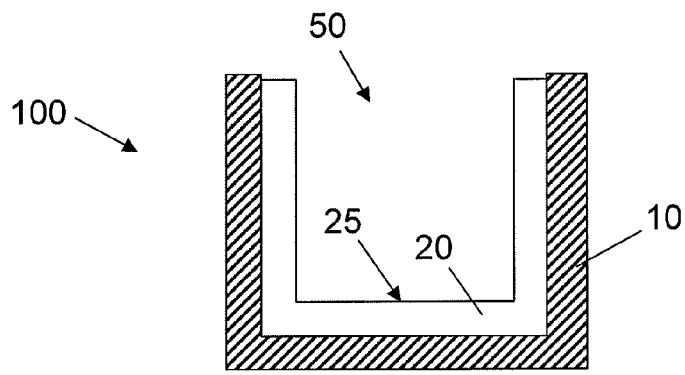

Article 100, in numerous embodiments, is cell culture ware having a well, such as a petri dish, a multi-well plate, a flask, a beaker or other container having a well. Referring now to FIG. 2, article 100 formed from base material 10 may include one or more wells 50. Well 50 includes a sidewall 55 and a surface 15. Referring to FIG. 2B-C, a synthetic polymer coating 20 may be disposed on surface 15 or sidewalls 55 (or, as discussed above with regard to FIG. 1 one or more intermediate layer 30 may be disposed between surface 15 or sidewall 55 and synthetic polymer coating 20) or a portion thereof.

In various embodiments, article 100 includes a uniformly coated layer 20 having a surface 25 with an area greater than about 5 mm$^2$. When the area of the surface 15 is too small, reliable cell responses may not be readily observable because some cells, such as human embryonic stem cells, are seeded as colonies or clusters of cells (e.g., having a diameter of about 0.5 mm) and adequate surface is desirable to ensure attachment of sufficient numbers of colonies to produce a quantitative cell response. In numerous embodiments, an article 100 has a well 50 having a uniformly coated surface 15, where the surface 15 has an area greater than about 0.1 cm$^2$, greater than about 0.3 cm$^2$, greater than about 0.9 cm$^2$, or greater than about 1 cm$^2$.

2. Coating of Synthetic Polymer Layer

A synthetic polymer layer may be disposed on a surface of a cell culture article via any known or future developed process. Preferably, the synthetic polymer layer provides a uniform layer that does not delaminate during typical cell culture conditions. The synthetic polymer surface may be associated with the base material substrate via covalent or non-covalent interactions. Examples of non-covalent interactions that may associate the synthetic polymer surface with the substrate include chemical adsorption, hydrogen bonding, surface interpenetration, ionic bonding, van der Waals forces, hydrophobic interactions, dipole-dipole interactions, mechanical interlocking, and combinations thereof.

In various embodiments, the base material substrate surface is coated according to the teachings of co-pending application Ser. No. 61/062,891, filed on Jan. 30, 2008, naming Gehman et al. as inventors, and entitled STEM CELL CULTURE ARTICLE AND SCREENING, which is hereby incorporated herein by reference in its entirety for all purposes to the extent that it does not conflict with the disclosure presented herein.

In numerous embodiments, monomers are deposited on a surface of a cell culture article and polymerized in situ. In such embodiments, the base material will be referred to herein as the "substrate" on which the synthetic polymer material is deposited. Polymerization may be done in solution phase or in bulk phase.

As many of the monomers identified in Table 1 above are viscous, it may be desirable to dilute the monomers in a suitable solvent to reduce viscosity prior to being dispensed on the surface. Reducing viscosity may allow for thinner and more uniform layers of the synthetic polymer material to be formed. One of skill in the art will be able to readily select a suitable solvent. Preferably the solvent is compatible with the material forming the cell culture article and the monomers. It may be desirable to select a solvent that is non-toxic to the cells to be cultured and that does not interfere with the polymerization reaction. Alternatively, or in addition, selection of a solvent that can be substantially completely removed or removed to an extent that it is non-toxic or no longer interferes with polymerization may be desirable. In additional embodiments, it may be desirable to select solvents which do not interact with the substrate. Further, it may be desirable that the solvent be readily removable without harsh conditions, such as vacuum or extreme heat. Volatile solvents are examples of such readily removable solvents. As described in co-pending application Ser. No. 61/062,891, ethanol may be a particularly suitable solvent when it is desired to remove solvent prior to polymerization.

The monomers may be diluted with solvent by any suitable amount to achieve the desired viscosity and monomer concentration. Generally the monomer compositions used according to the teachings presented herein contain between about 0.1% to about 99% monomer. By way of example, the monomer may be diluted with an ethanol solvent to provide a composition having between about 0.1% and about 50% monomer, or from about 0.1% to about 10% monomer by volume. The monomers may be diluted with solvent so that the polymer layer 20 achieves a desired thickness. As discussed above, if the deposited monomers are too thick, an uneven surface may result. As described in further details in the Examples, uneven surfaces may be observed when the monomer-solvent composition is deposited on a surface 15 of a well 50 at a volume of greater than about 8 microliters per square centimeter of the surface 15. In various embodiments, the monomer-solvent compositions are deposited on a surface 15 of a well 50 in a volume of about 7 microliters or less per square centimeter of the surface 15. For example, the monomer-solvent compositions may be deposited on a surface 15 of a well 50 in a volume of about 5 microliters or less per square centimeter of the surface 15, or about 2 microliters or less per square centimeter of the surface 15.

In various embodiments, article 100 includes a uniformly coated layer 20 having a surface 25 with an area greater than about 5 mm$^2$. When the area of the surface 15 is too small, reliable cell responses may not be readily observable because some cells, such as human embryonic stem cells, are seeded as colonies or clusters of cells (e.g., having a diameter of about 0.5 mm) and adequate surface is desirable to ensure attachment of sufficient numbers of colonies to produce a quantitative cell response. In numerous embodiments, an article 100 has a well 50 having a uniformly coated surface 15, where the surface 15 has an area greater than about 0.1 cm$^2$, greater than about 0.3 cm$^2$, greater than about 0.9 cm$^2$, or greater than about 1 cm$^2$.

In various embodiments, synthetic polymer surface is deposited on a surface of an intermediate layer that is associated with the base material via covalent or non-covalent interactions, either directly or via one or more additional intermediate layers (not shown). In such embodiments, the intermediate layer will be referred to herein as the "substrate" onto which the synthetic polymer surface is deposited.

In various embodiments, the surface of the base material is treated. The surface may be treated to improve binding of the synthetic polymer surface to the base material surface, to facilitate monomer spreading on the base material surface, or the like. Of course, the base material may be treated for similar purposes with regard to an intermediate layer. In various embodiments, the surface is corona treated or vacuum plasma treated. High surfaces energy obtainable from such treatments may facilitate monomer spreading and uniform coating. Examples of vacuum plasma treatment that may be employed include microwave vacuum plasma treatments and radio frequency vacuum plasma treatments. The vacuum plasma treatments may be performed in the presence of reactive gases, such as oxygen, nitrogen, ammonia or nitrous oxide.

To form the synthetic polymer surface, one or more monomers presented in Table 1 above are polymerized. If one monomer is used, the polymer will be referred to as a homopolymer of the monomer. If two or more different monomers are used, the polymer will be referred to as a copolymer of the monomers. The monomers employed may be monofunctional, difunctional, or higher-functional. When two or more monomers are used, the ratio of the monomers may be varied. In various embodiments, two monomers are used and the ratio, by volume of the first monomer to the second monomer ranges from between about 5:95 to about 95:5. For example, the ratio of the first monomer to the second monomer ranges from between about 10:90 to about 90:10, about 20:80 to about 80:20, from about 30:70 to about 70:30. In some embodiments, the ratio of the first monomer to the second monomer is about 50:50, 30:70, or 10:90. It will be understood that the degree of cross-linking of the polymer may be controlled by varying the concentration of monomers or the ratios of difunctional or higher-functional monomers to monofunctional monomers. Increased concentrations of difunctional or higher-functional monomers will increase the degree of cross-linking in the chains.

In addition to the monomers that form the polymer layer, a composition forming the layer may include one or more additional compounds such as surfactants, wetting agents, photoinitiators, thermal initiators, catalysts, activators, and cross-linking agents.

Any suitable polymerization initiator may be employed. One of skill in the art will readily be able to select a suitable initiator, e.g. a radical initiator or a cationic initiator, suitable for use with the monomers listed in Table 1. In various embodiments, UV light is used to generate free radical monomers to initiate chain polymerization.

Any suitable initiator may be used. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, or mixtures thereof. Examples of suitable commercially available, ultraviolet-activated and visible light-activated photoinitiators have tradenames such as IRGACURE 651, IRGACURE 184, IRGACURE 369, IRGACURE 819, DAROCUR 4265 and DAROCUR 1173 commercially available from Ciba Specialty Chemicals, Tarrytown, N.Y. and LUCIRIN TPO and LUCIRIN TPO-L commercially available from BASF (Charlotte, N.C.)

A photosensitizer may also be included in a suitable initiator system. Representative photosensitizers have carbonyl groups or tertiary amino groups or mixtures thereof. Photosensitizers having a carbonyl group include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethyl-ethanolamine, and dimethylamino-ethylbenzoate. Commercially available photo sensitizers include QUANTICURE ITX, QUANTICURE QTX, QUANTICURE PTX, QUANTICURE EPD from Biddle Sawyer Corp.

In general, the amount of photosensitizer or photoinitiator system may vary from about 0.01 to 10% by weight.

Examples of cationic initiators include salts of onium cations, such as arylsulfonium salts, as well as organometallic salts such as ion arene systems.

In various embodiments where the monomers are diluted in solvent before being deposited on the substrate surface, the solvent is removed prior to polymerizing. The solvent may be removed by any suitable mechanism or process. As described in copending application Ser. No. 61/062,891, it has been found that removal of substantially all of the solvent prior to curing, allows for better control of curing kinetics and the amount of monomer converted. When conversion rates of the monomers are increased, waste generation and cytotoxicity are reduced.

Whether polymerized in bulk phase (substantially solvent free) or solvent phase, the monomers are polymerized via an appropriate initiation mechanism. Many of such mechanisms are well known in the art. For example, temperature may be increased to activate a thermal initiator, photoinitiators may be activated by exposure to appropriate wavelength of light, or the like. According to numerous embodiments, the monomer or monomer mixture is cured using UV light. The curing preferably occurs under inert gas protection, such as nitrogen protection, to prevent oxygen inhibition. Suitable UV light combined with gas protection may increase polymer conversion, insure coating integrity and reduce cytotoxicity.

The cured synthetic polymer layer may be washed with solvent one or more times to remove impurities such as unreacted monomers or low molecular weight polymer species. In various embodiments, the layer is washed with an ethanol solvent, e.g. 70% ethanol, greater than about 90% ethanol, greater than about 95% ethanol, or greater than about 99% ethanol. Washing with an ethanol solvent may not only serve to remove impurities, which may be cytotoxic, but also can serve to sterilize the surface prior to incubation with cells.

3. Incubating Cells on Synthetic Polymer Layer

Stem cell-derived OPCs may be cultured on a synthetic polymer layer, as described above, according to any suitable protocol. As used herein, "stem cell derived OPC" means an OPC obtained from differentiation of a stem cell. In some embodiments, the stem cells are multipotent, totipotent, or pluripotent stem cells. The stem cells may be present in an organ or tissue of a subject. In numerous embodiments, the stem cells are embryonic stem cells, such as human embryonic stem cells. As used herein, "OPC" or "oligodendrocyte progenitor cell" means precursor cells to myelin-forming oligodendrocytes.

Because human embryonic stem cells (hESC) have the ability to grown continually in culture in an undifferentiated state, the hESC for use in this invention may be obtained from an established cell line. Examples of human embryonic stem cell lines that have been established include, but are not limited to, H1, H7, H9, H13 or H14 (available from WiCell established by the University of Wisconsin) (Thompson (1998) Science 282:1145); hESBGN-01, hESBGN-02, hES-BGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells used in the invention may also be obtained directly from primary embryonic tissue. Typically this is done using frozen in vitro fertilized eggs at the blastocyst stage, which would otherwise be discarded.

OPCs according to the invention may also be differentiated from induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm and thus are suitable for differentiation into OPCs. The iPS cells, like hESC, also form teratomas when injected into immuno-deficient mice, e.g., SCID mice. (Takahashi et al., (2007) Cell 131(5):861; Yu et al., (2007) Science 318:5858).

Stem cell derived OPCs may be obtained by any suitable methods. One way to obtain such cells is described in Zhang et al., "Oligodendrocyte progenitor cells derived from human embryonic stem cells express neurotrophic factors, Stem Cells and Development, 15: 943-952 (2006), citing Nistor et al., Human embryonic stem cells differentiate into oligodendrocytes in high purity and mylenate after spinal cord transplantation, Glia 49: 385-396 (2005). Briefly, undifferentiated human embryonic stem cells, such as those derived from the H1 or H7 human embryonic stem cell lines, may be cultured on MATRIGEL-coated plates in mouse embryonic fibroblast (MEF) conditioned medium (CM) supplemented with about 8 ng/ml fibroblast growth factor-2 (FGF-2) or in a chemically defined medium, such as X-VIVO 10 from Cambrex, supplemented with about 80 ng/ml FGF-2 and 0.5 ng/ml transforming growth factor-β1 (TGF-β1). To induce differentiation, the protocol described by Nistor et al. may be employed. Briefly, the human embryonic stem cells may be collagenase digested, scraped, and cultured in defined medium supplemented with insulin, transferrin, progesterone, putrescin, selenium, triiodothyroidin and B27 for 28 days on an ultra-low-attachment plate. The cells may then be cultured in the defined medium for an additional 14 days on growth-factor reduced MATRIGEL. The cells may then be treated with FGF-2, epidermal growth factor (EGF) and all-trans retinoic acid on specified days during differentiation. Differentiation may occur over a number of days, such as 42 days. Of course, any other suitable method may be employed.

Prior to seeding cells, the cells may be harvested and suspended in a suitable medium, such as a growth medium in which the cells are to be cultured once seeded onto the surface. For example, the cells may be suspended in and cultured in serum-containing medium, a conditioned medium, or a chemically-defined medium. As used herein, "chemically-defined medium" means cell culture media that contains no components of unknown composition. Chemically defined media may, in various embodiments, contain no proteins, hydrosylates, or peptides of unknown composition. In some embodiments, conditioned media contains polypeptides or proteins of known composition, such as recombinant growth hormones. Because all components of chemically-defined media have a known chemical structure, variability in culture conditions and thus cell response can be reduced, increasing reproducibility. In addition, the possibility of contamination is reduced. Further, the ability to scale up is made easier due, at least in part, to the factors discussed above.

The cells may be seeded at any suitable concentration. Typically, the cells are seeded at about 10,000 cells/cm$^2$ of substrate to about 500,000 cells/cm$^2$. For example, cells may be seeded at about 50,000 cells/cm$^2$ of substrate to about 150,000 cells/cm$^2$. However, higher and lower concentrations may readily be used. The incubation time and conditions, such as temperature $CO_2$ and $O_2$ levels, growth medium, and the like, will depend on the nature of the cells being cultured and can be readily modified. The amount of time that the cells are incubated on the surface may vary depending on the cell response being studied or the cell response desired.

Any suitable method may be used, if desired, to confirm that the stem cell derived OPCs are indeed OPCs or that the stem cells employed have successfully differentiated into OPCs. For example, the presence of certain OPC-selective markers may be investigated. Such markers include Nestin, Oligo1, platelet derived growth factor receptor alpha (PDG-FRα) and NG2. Antibodies to such markers may be used in standard immunocytochemical or flow cytometry techniques. In addition or alternatively, cellular morphology or production of growth factors detectable in the medium may be evaluated. For example, cultured OPCs may produce one or more of activin A, HGF, midkine, and TGF-β2, which may be detectable in the culture medium via standard assays, such as ELISA.

The cultured stem cell derived OPCs may be used for any suitable purpose, including investigational studies in culture, in animals, for developing therapeutic uses, or for therapeutic purposes. One potential therapeutic or investigational purpose is repairing damage due to spinal cord injury.

In the following, non-limiting examples are presented, which describe various embodiments of the articles and methods discussed above.

EXAMPLES

Example 1

Identification of Acrylic Coating Surfaces Suitable for Culturing Stem Cell Derived OPCs in a Chemically Defined Medium 1. Coating Preparation Acrylic coating surfaces were prepared from homomonomers or copolymers of various acrylate monomers. For copolymers two different acrylate monomers were used. A total of 24 homopolymer and 552 copolymer combinations were applied in wells. Briefly, the monomers were diluted in ethanol, and IRGACURE 819 photoinitiator to the ratio of 1:9:0.01 (monomer[volume]/ethanol[volume]/photoinitiator [weight]) to prepare the formulation. For copolymers, two different monomers were mixed with the volume ratio of 70:30 or 30:70. In copolymer formulation, total monomers [volume]/ethanol[volume]/photoinitiator[weight] still remain the ratio of 1:9:0.01. The formulations were placed in a well of a plasma treated cyclic olefin copolymer 96 well plates (provided by Corning Life Science development group) at a volume of 5 μL using BioTek Precession Microplate Pipetting System. Each well received a predetermined homopolymer or copolymer combination, with some wells being coated with MATRIGEL as a positive control. For the wells coated with acrylate monomers, the ethanol solvent was removed by evaporation at room temperature for 3 hr, which removes >99% of the ethanol. The coatings were then cured with 13 mW/cm$^2$ pulsed (100 Hz) UV light (Xenon RC-801) for 1 min in N$_2$ purged box (with fused silica window). After curing, a washing step was taken. Briefly, the surface in each well of 96-well plates was incubated with 200 μL of >99% ethanol for 1 hr followed by 200 μL of water for over night to move potential extractables. Finally the surfaces were air dried before sterilization.

2. Cell Preparation and Assays

For hESC-derived OPC, H1 hESC colonies were detached using 200 U/ml collagenase IV and transferred to Corning ultra-low-adhesion (ULA) plates to allow the formation of embryoid bodies (EBs). To induce neural differentiation, EBs were treated with epidermal growth factor (EGF), FGF-2 (fibroblast growth factor-2) and retinoic acid (RA) for 9 days following by 18 days treatment with EGF only. (Base medium: defined medium supplemented with insulin, transferrin, progesterone, putrescin, selenium, triiodothyroidin (Sigma), and B27 (Invitrogen)).

At this point two different acrylate re-plating schedules were tested: In the first protocol, on day 28, EBs were re-plated on different acrylic surfaces in 96-well plate or on MATRIGEL-coated wells as positive control. Seven days later (day 35), cells were fixed with 4% PFA. In the second protocol, on day 28, EBs were re-plated on MATRIGEL, cultured for 7 days and then (day 35) re-plated on different acrylic surfaces in 96-well plate or on MATRIGEL-coated wells as positive control. Seven days later (day 42), cells were fixed with 4% PFA.

Cells from the both protocols were immunostained for OPC-specific markers, Nestin, Olig1, and counterstained with 4'-6-Diamidino-2-phenylindole DAPI (nuclear stain).

After scanning each plate with ArrayScan, the following quantitative analyses were performed for the each surface: 1) TNC: total number of cells, based on DAPI positive cell number, 2) TNO: total number of OPC, based on olig1-positive cells.

3. Results

Figure 3:
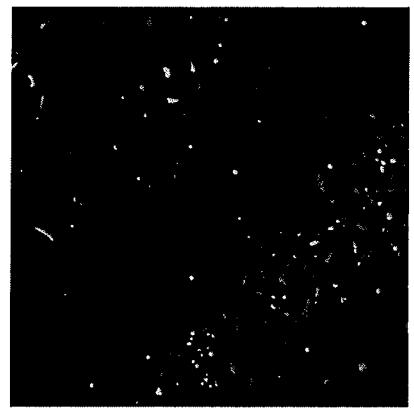
FIGS. 3A-C are fluorescence images of immunostained hES cell-derived OPCs after replating on acrylate coating surface 123-2 (A) and 95-2 (B), and positive control surface Matrigel (C) between 28-day and 35-day. OPCs derived from human ES cells were immunostained for the OPC marker, Olig1 (green) and nestin (red).
Figure 3:
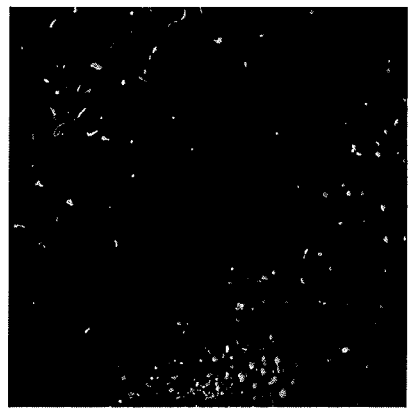
Figure 3:
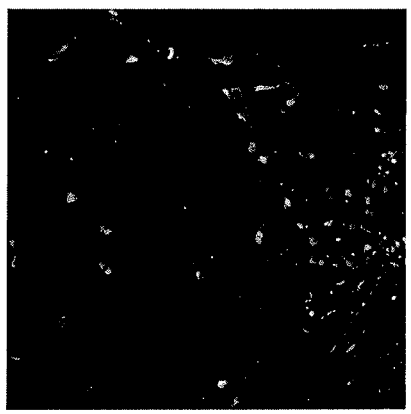
Figure 4:
FIGS. 4A-C are fluorescence images of immunostained hES cell-derived OPCs after replating on acrylate coated surface 123-2 (A), 122-3 (B) and Matrigel™ (C) between 28-day and 35-day as well as between 35-day and 42-day. OPCs derived from human ES cells were immunostained for the OPC marker, Olig1 (green) and nestin (red).
Figure 4:
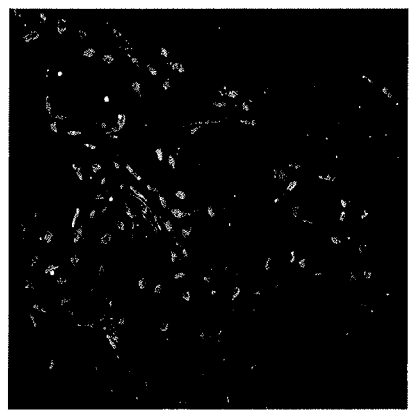
Figure 4:
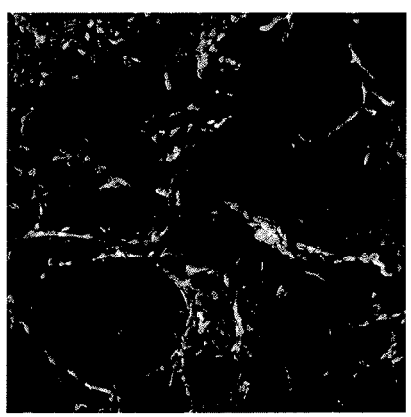
Figure 5A:
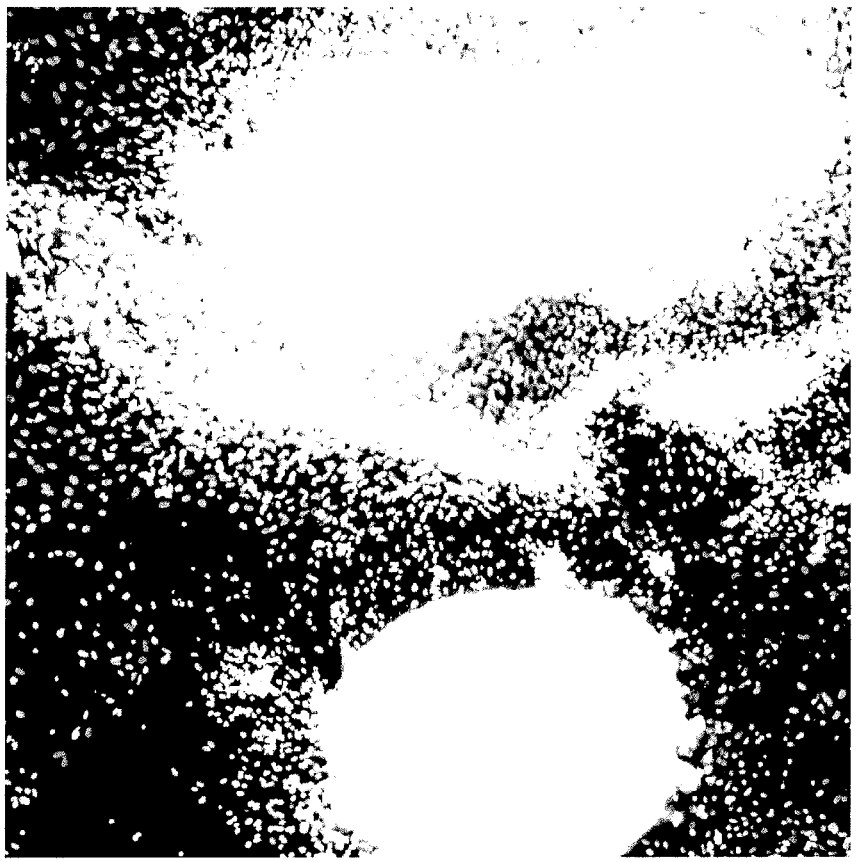
FIGS. 5A-F are fluorescence images of hES cell-derived OPCs on Matrigel™ (A) and on acrylate coated surfaces 22-2 (B), 22-3 (C), 133-4 (D), 24-10 (E), and 72-2 (F).
Figure 5B:
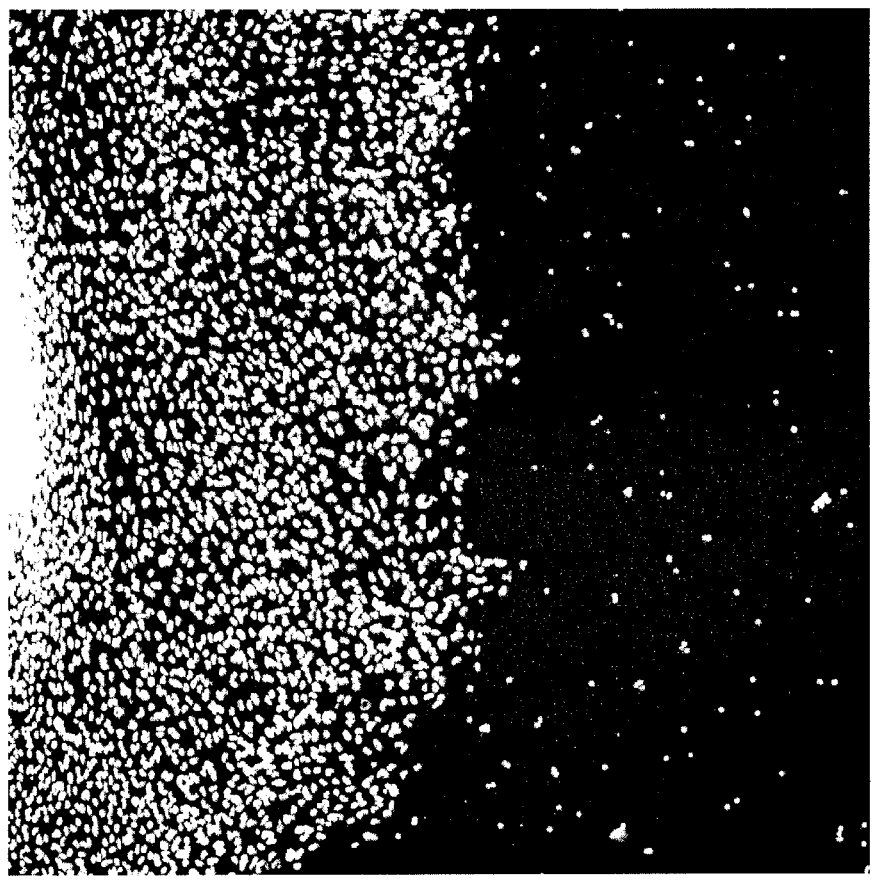
Figure 5C:
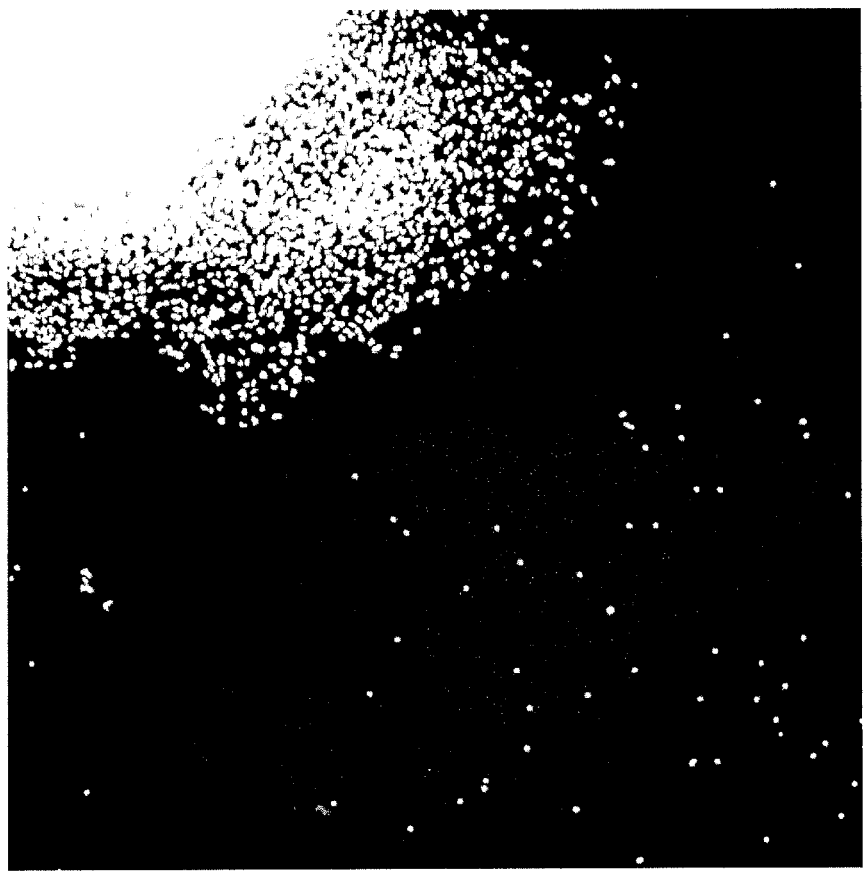
Figure 5D:
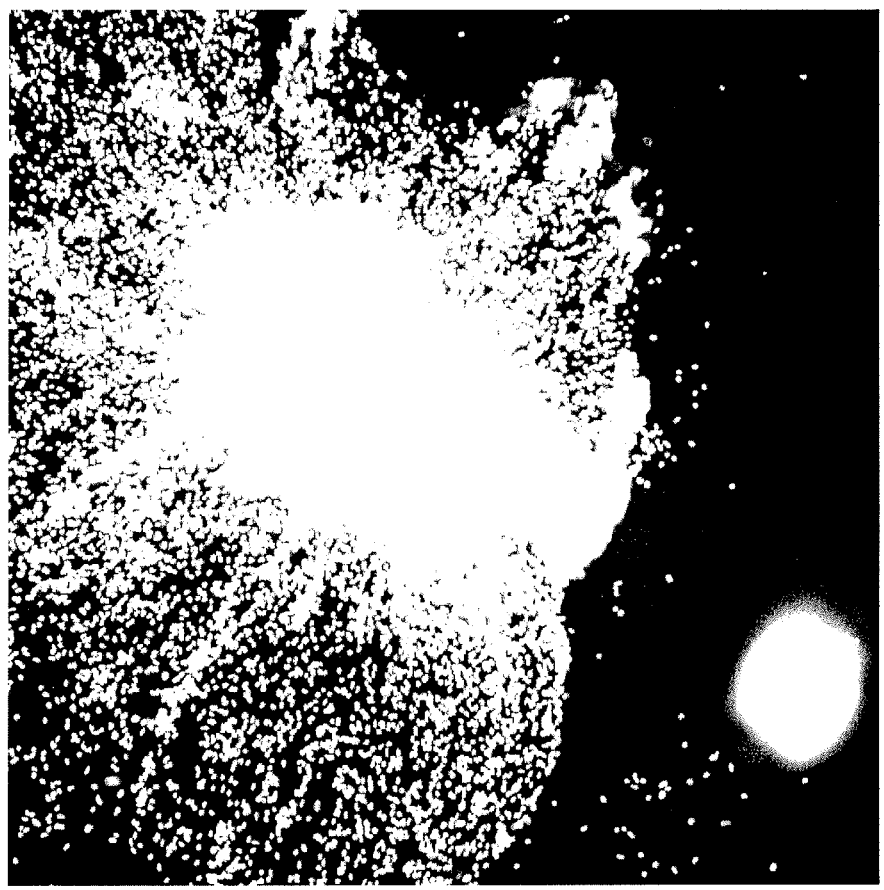
Figure 5E:
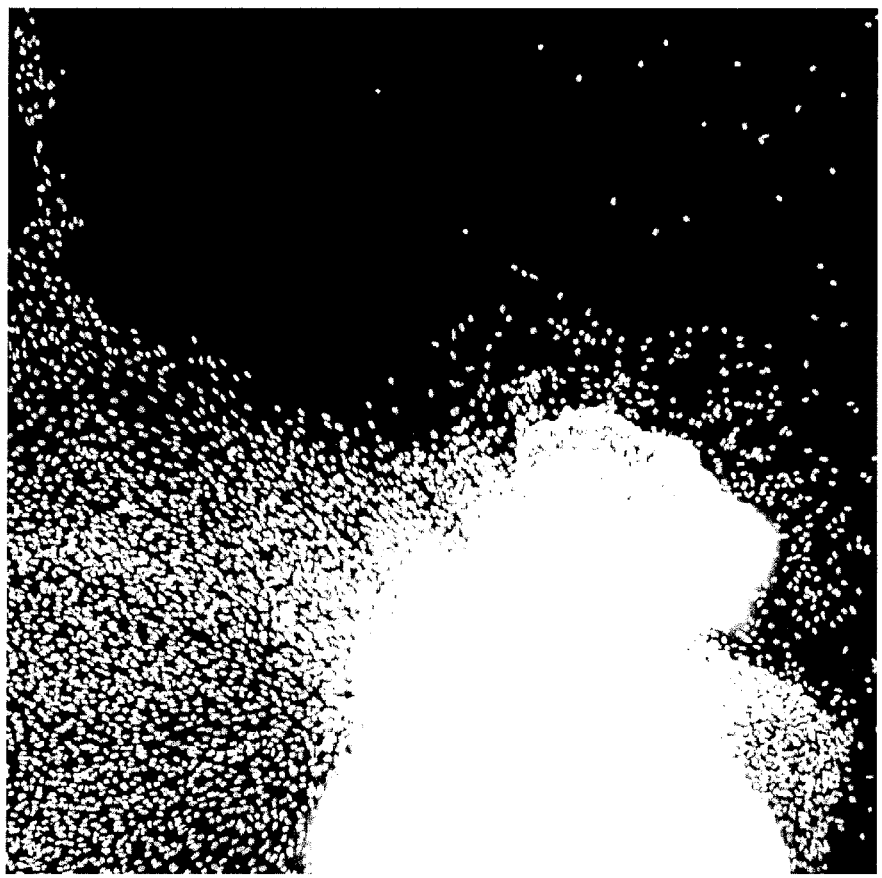
Figure 5F:
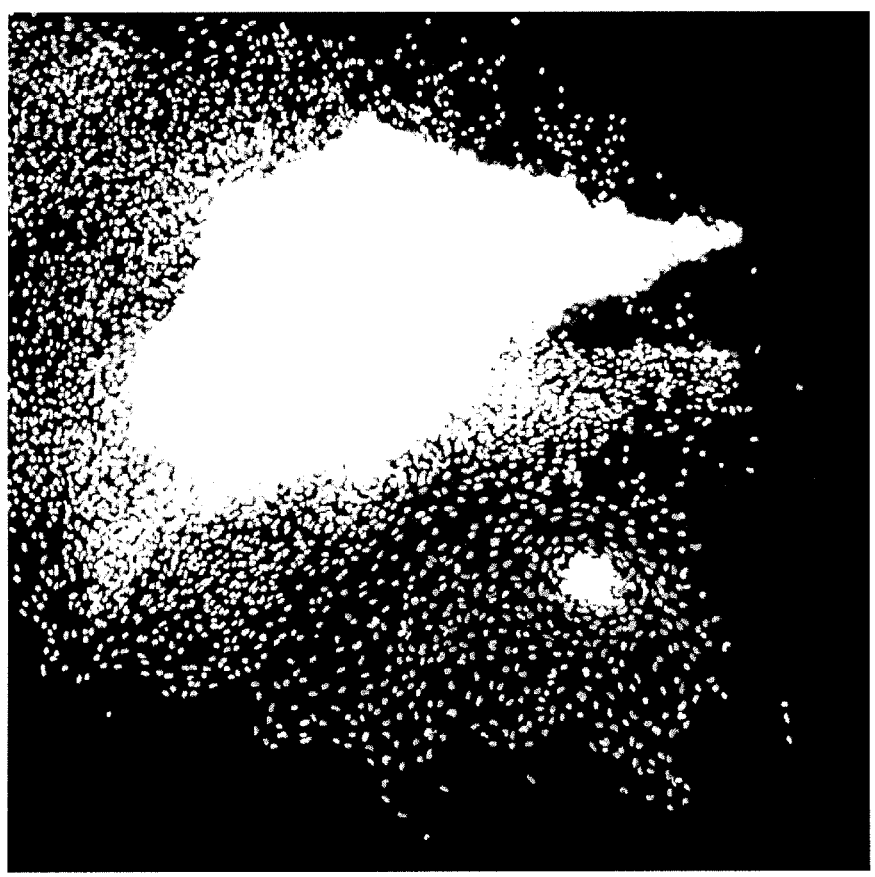

It was found that only a small portion of the tested surfaces supported attachment and cell outgrowth from EBs in chemically defined medium. FIG. 3 are fluorescence images of immunostained hES cell-derived OPC after re-plating on selected acrylate coated surfaces and positive control Matrigel surface between 28-day and 35-day for differentiation. FIG. 4 are fluorescence images of immunostained hES cell-derived OPC after two re-platings on selected acrylate coated surfaces and positive control Matrigel surface between 28-day and 35-day, as well as between 35-day and 42-days for differentiation. The immunostaining images showed that differentiated cells expressed the OPC markers on some acrylate coating surfaces. The staining of the cells grown on the acrylate surfaces was similar to the staining observed in the cells grown on the Martigel control surface. Examples of the coating surfaces which supported differentiated human OPCs in chemically defined medium are listed in Table 2, where the volume ratio of monomer (1) to monomer (2) is 70:30.

TABLE 2

Example compositions of acrylic polymers which support the culture of hES cell derived OPCs in chemically defined medium.

| Polymer ID | Monomer (1) | Monomer (2) |
|---|---|---|
| 95-1 | Tetra(ethylene glycol) diacrylate | |
| 27-1 | Tetra(ethylene glycol) diacrylate | Neopentyl glycol ethoxylate diacrylate |
| 123-1 | Glycerol dimethacrylate | Tetra(ethylene glycol) diacrylate |
| 123-2 | Glycerol dimethacrylate | Tri(ethylene glycol) dimethacrylate |
| 22-1 | Glycerol dimethacrylate | Di(ethylene glycol) dimethacrylate |
| 22-2 | Glycerol dimethacrylate | Tetraethylene glycol dimethacrylate |
| 22-3 | Glycerol dimethacrylate | 1,6-Hexanediol propoxylate diacrylate |
| 24-10 | Glycerol dimethacrylate | 1,6-Hexanediol ethoxylate diacrylate |
| 28-2 | Tri(ethylene glycol) dimethacrylate | Trimethylolpropane triacrylate |
| 28-10 | 1,4-Butanediol dimethacrylate | 1,9 nonanediol diacrylate |
| 36-4 | 1,6-Hexanediol diacrylate | Tricyclo[5.2.1.0$^{2,6}$]decanedimethanol diacrylate |
| 36-5 | 1,6-Hexanediol diacrylate | 1,6-Hexanediol ethoxylate diacrylate |
| 36-6 | 1,6-Hexanediol diacrylate | Neopentyl glycol ethoxylate diacrylate |
| 39-6 | Neopentyl glycol propoxylate (1PO/OH) diacrylate | Neopentyl glycol ethoxylate diacrylate |
| 133-4 | Di(ethylene glycol) dimethacrylate | Neopentyl glycol diacrylate |
| 47-4 | Di(ethylene glycol) dimethacrylate | Tricyclo[5.2.1.0$^{2,6}$]decanedimethanol diacrylate |
| 41-9 | Tetra(ethylene glycol) dimethacrylate | 1,4-Butanediol dimethacrylate |
| 50-6 | Tetra(ethylene glycol) dimethacrylate | Neopentyl glycol ethoxylate diacrylate |

TABLE 2-continued

Example compositions of acrylic polymers which support the culture of hES cell derived OPCs in chemically defined medium.

| Polymer ID | Monomer (1) | Monomer (2) |
|---|---|---|
| 51-1 | 1,6-Hexanediol propoxylate diacrylate | Neopentyl glycol ethoxylate diacrylate |
| 49-4 | Neopentyl glycol diacrylate | Tricyclo[5.2.1.0$^{2,6}$]decanedimethanol diacrylate |
| 49-5 | Neopentyl glycol diacrylate | 1,6-Hexanediol ethoxylate diacrylate |
| 52-4 | Neopentyl glycol diacrylate | Poly(propylene glycol) diacrylate |
| 63-3 | Trimethylolpropane ethoxylate (1 EO/OH) methyl diacrylate | 2,2,3,3,4,4,5,5 octafluoro 1,6 hexanediol diacrylate |
| 71-1 | Neopentyl glycol ethoxylate diacrylate | Di(ethylene glycol) dimethacrylate |
| 65-9 | Trimethylolpropane triacrylate | 1,4-Butanediol dimethacrylate |
| 71-6 | Trimethylolpropane triacrylate | Di(ethylene glycol) dimethacrylate |
| 71-10 | Trimethylolpropane triacrylate | Neopentyl glycol diacrylate |
| 74-6 | Trimethylolpropane triacrylate | Neopentyl glycol dimethacrylate |
| 72-2 | 2,2,3,3,4,4,5,5 octafluoro 1,6 hexanediol diacrylate | Tetra(ethylene glycol) dimethacrylate |
| 72-5 | 2,2,3,3,4,4,5,5 octafluoro 1,6 hexanediol diacrylate | Neopentyl glycol diacrylate |
| 72-9 | Poly(propylene glycol) diacrylate | Glycerol 1,3-diglycerolate diacrylate |

FIGS. 5A-F show images taken from micrographs of hESC derived OPCs growing on Matrigel™ as a positive control and selected embodiments of surfaces of the present invention; 22-2 (B), 22-3 (C), 133-4 (D), 24-10 (E), and 72-2 (F). FIGS. 5A-F show nuclear staining on hESC derived OPCs on Matrigel or the above-referenced embodiments of surfaces of the present invention stained with Hoecst nuclear stain. FIGS. 5A-F illustrate that embodiments of surfaces of the present invention provide suitable surfaces to support adhesion and growth of hESC derived OPCs in chemically defined medium. For other tested homopolymers and copolymer combinations, that is those combinations that are not listed in Table 2 above, no EB attachment to the surface or cell outgrows from the EBs was observed.

Thus, embodiments of SYNTHETIC SURFACES FOR CULTURING STEM CELL DERIVED OLIGODENDROCYTE PROGENITOR CELLS are disclosed. One skilled in the art will appreciate that the arrays, compositions, kits and methods described herein can be practiced with embodiments other than those disclosed. The disclosed embodiments are presented for purposes of illustration and not limitation.

What is claimed is:

1. A cell culture comprising 1) an oligodendrocyte progenitor cell disposed on a polymer material, wherein the polymer material comprises an acrylate or a diacrylate; and 2) a culture medium.

2. The cell culture of claim 1, wherein the oligodendrocyte progenitor cell is a human oligodendrocyte progenitor cell.

3. The cell culture of claim 1, wherein the oligodendrocyte progenitor cell is derived from a human embryonic stem cell.

4. The cell culture of claim 1, wherein the oligodendrocyte progenitor cell is derived from an induced pluripotent stem cell.

5. A cell culture comprising 1) a progenitor cell expressing Nestin and Olig1 disposed on a polymer material, wherein the polymer material comprises an acrylate or a diacrylate; and 2) a culture medium.

6. The cell culture of claim 5, wherein the progenitor cell is a human oligodendrocyte progenitor cell.

7. The cell culture of claim 5, wherein the progenitor cell is derived from a human embryonic stem cell.

8. The cell culture of claim 5, wherein the progenitor cell is derived from an induced pluripotent stem cell.

* * * * *